US009504711B2

(12) United States Patent
Benedetti et al.

(10) Patent No.: US 9,504,711 B2
(45) Date of Patent: Nov. 29, 2016

(54) ZINC-ENRICHED BIOMASS, METHOD FOR THE PREPARATION THEREOF AND PRO-BIOTIC, COSMETIC, DIETARY AND NUTRACEUTIC PRODUCTS COMPRISING THE SAME

(71) Applicant: BIOMAN S.R.L., Turin (IT)

(72) Inventors: Alberto Benedetti, Cernusco Sul Naviglio (IT); Francesco Girardo, Orbassano (IT)

(73) Assignee: BIOMAN S.R.L., Turin (IT)

( * ) Notice: Subject to any disclaimer, the term of this patent is extended or adjusted under 35 U.S.C. 154(b) by 0 days.

(21) Appl. No.: 14/071,593

(22) Filed: Nov. 4, 2013

(65) Prior Publication Data
US 2014/0161781 A1 Jun. 12, 2014

Related U.S. Application Data

(63) Continuation of application No. 12/670,504, filed as application No. PCT/IB2008/052943 on Jul. 22, 2008, now Pat. No. 8,597,638.

(30) Foreign Application Priority Data

Jul. 26, 2007 (IT) ............................. TO2007A0555

(51) Int. Cl.
*A01N 63/00* (2006.01)
*A61K 33/30* (2006.01)
*A23L 1/30* (2006.01)
*A23L 1/304* (2006.01)
*A61K 8/99* (2006.01)
*A61K 35/744* (2015.01)
*A61K 35/745* (2015.01)
*A61Q 19/00* (2006.01)
*C12N 1/20* (2006.01)
*C12R 1/01* (2006.01)
*C12R 1/46* (2006.01)

(52) U.S. Cl.
CPC ............ *A61K 33/30* (2013.01); *A23L 1/304* (2013.01); *A23L 1/3014* (2013.01); *A61K 8/99* (2013.01); *A61K 35/744* (2013.01); *A61K 35/745* (2013.01); *A61Q 19/00* (2013.01); *C12N 1/20* (2013.01); *C12R 1/01* (2013.01); *C12R 1/46* (2013.01); *A23V 2002/00* (2013.01)

(58) Field of Classification Search
None
See application file for complete search history.

(56) References Cited

U.S. PATENT DOCUMENTS

| 3,661,713 A | 5/1972 | McMullen |
| 8,597,638 B2 | 12/2013 | Benedetti et al. |
| 2007/0009502 A1 | 1/2007 | Lall et al. |
| 2007/0258964 A1 | 11/2007 | Andreoni et al. |

FOREIGN PATENT DOCUMENTS

| CA | 2525342 | 4/2006 |
| JP | 60075279 | 4/1985 |
| JP | 6-508516 | 9/1994 |
| JP | 2003-250528 | 9/2003 |
| JP | 2010-534470 | 11/2010 |
| KR | 2003025587 | 3/2003 |
| RU | 2002/117254 | 1/2004 |
| WO | 92/21749 | 12/1992 |
| WO | 00/07606 | 2/2000 |
| WO | 2006/112998 | 10/2006 |
| WO | 2007/029773 | 3/2007 |
| WO | 2009/013709 | 1/2009 |

OTHER PUBLICATIONS

Homer et al. "Distribution of zinc-tolerant bacteria in stream sediments". Hydrobiologia. 1985, 128:155-160.*
PCT International Search Report mailed on Jan. 16, 2009 for PCT/IB2008/052943 filed on Jul. 22, 2008 in the name of Bioman S.R.L.
PCT Written Opinion mailed on Jan. 16, 2009 for PCT/IB2008/052943 filed on Jul. 22, 2008 in the name of Bioman S.R.L.
ATCC Catalogue. ATCC Bacteria and Bacteriophages. 19$^{th}$ edition, 1996, pp. 68, 352, 477 and 497.
Gerhardt, P., "Manual of Method for General Bacteriology", American Society for Microbiology. 1981, pp. 210-213.
Japanese Office Action from Japanese Application 2010-517531, mailed on Mar. 12, 2013 (with English translation).
Babich, H. et al. "Toxocity of Zinc to Fungi, Bacteria, and Coliphages: Influence of Chloride Ions". Applied and Environmental Microbiology, Dec. 1978, 36(6):906-914.
Mehrotra and Sumbali, (Excerpt) "Principles of Microbiology:M &S". Tata McGraw-Hill Education, 2009; p. 146.
David Evans Reisner, (Excerpt) "Bionanotechnology II: Global Prospects". CRC Press, 2011; pp. 350-353.
Lee, A.J. et al. "The ability of zinc to inhibit the sporulation and viability of Clostridium sporogenes and growth of other bacteria". International Journal of Food Science and Technology. 2011. 46:1494-1501.
Nweke, C.O. "Kinetics of zinc toxicity to environmental bacterial isolates". Revista Ambiente & Agua—An Interdisciplinary Journal of Applied Science: v. 4, n. 3, 2009.

(Continued)

*Primary Examiner* — Vera Afremova
(74) *Attorney, Agent, or Firm* — Steinfl & Bruno LLP

(57) ABSTRACT

The invention relates to a zinc-enriched biomass comprising living or subsequently killed micro-organisms, selected from the group consisting of *Streptococcus thermophilus* and *Bifidobacterium animalis* subsp. *lactis* and combinations thereof, a method for the manufacture of said zinc-enriched biomass, as well as food preparations, nutraceutic products, functional foods, cosmetic and cosmeceutic products, and food supplements, comprising the said biomass. Furthermore, new micro-organism strains are described which are able to concentrate zinc within the cell in very high amounts and therefore are particularly suitable for use in the method of the invention.

15 Claims, 2 Drawing Sheets

(56) References Cited

OTHER PUBLICATIONS

Briczinksi et al., "Strain-Specific Genotyping of *Bifidobacterium animalis* subsp. *lactis* by Using Single-Nucleotide Polymorphisms, Insertions, and Deletions", Applied and Environmental Microbiology, 2009, vol. 75, No. 23, pp. 7501-7508.

Giraffa et al., "Genotypic and phenotypic heterogeneity of *Steptococcus thermophilus* strains isolated from dairy products", Journal of Applied Microbiology, 2001, vol. 91, pp. 937-943.

Mogna et al., "Selenium and Zinc Internalized by *Lactobacillus buchneri* Lb26 (DSM 16341) and *Bifidobacterium lactis* Bb1 (DSM 17850): Improved Bioavailability Using a New Biological Approach", J Clin Gastroenterol, vol. 46, Supp. 1, Oct. 2012, pp. S41-S45.

"Nutrient enriched probiotic composition comprises betaine, pancreatin, *lactobacillus* sp. *bifidobacteria* sp. fructo-oligo saccharide, vitamin and mineral," Derwent, XP002320541 Abstract (2004), 1 page.

* cited by examiner

ZINC-ENRICHED BIOMASS, METHOD FOR THE PREPARATION THEREOF AND PRO-BIOTIC, COSMETIC, DIETARY AND NUTRACEUTIC PRODUCTS COMPRISING THE SAME

CROSS REFERENCE TO RELATED APPLICATIONS

The present application is a continuation of U.S. application Ser. No. 12/670,504 filed on Jan. 25, 2010 incorporated herein by reference in its entirety, which is a U.S. national stage of International Application PCT/IB2008/052943 filed on Jul. 22, 2008, which in turn, claims priority to Italian Patent Application No. TO2007A000555 filed on Jul. 26, 2007.

The present invention relates to a zinc-enriched biomass, a method for the preparation thereof, as well as foodstuffs, pro-biotic, dietary, nutraceutic and cosmetic products comprising the same. The invention further relates to bacterial strains suitable to be used in the method of the invention.

Zinc is an essential mineral that is present in organisms in amounts higher than those of any other oligoelement, with the exception of iron. It is linked to the normal absorption of vitamins and their activity, particularly the B-complex vitamins. It is a constituent element of a huge number of enzymes that play a role in digestion and metabolism, including carbonic anhydrase, required for tissue respiration. In the human body, zinc is especially found in bones, teeth, skin, liver, muscles and hair. Zinc is rapidly absorbed into the higher portion of the small intestine. Zinc also deposits itself in certain eye structures, prostate, spermatozoa, skin, hair, nails and is found in white blood cells too. These supplies are not easily usable, therefore the food has to contain sufficient quantities of it in order to meet the organism's requirements. It is indispensable for body growth, tissue repair, and for a normal immune response. It is also important for carbohydrate digestion and phosphorous metabolism. It participates in the synthesis of nucleic acid that controls the creation of various proteins in cells, it is important for vitamin absorption, it is useful in healing processes, and it inhibits the bacterial, yeast, and skin saprophyte lipases. Very many enzymes need zinc to be active, which is necessary for protein synthesis, for certain aspects of hormonal functions, for brain functions, sight, and taste. Furthermore, the alcohol dehydrogenase enzyme—involved in alcohol breakdown—contains zinc, therefore alcohol causes a loss of zinc. Zinc is used to reduce sebaceous secretions, in healing processes for internal and external wounds (it accelerates the healing of wounds), in therapies for acne and seborrhoeic dermatitis. This metal can promote hair re-growth in people who suffer from alopecia aerata totalis and be used in diabetes therapy, thanks to its regulatory effects on blood insulin. Adding zinc to insulin has been found to extend the effect of the hormone on blood sugar levels.

Zinc-deficiency causes serious disorders in all living beings. It is known that certain drugs can induce a zinc-deficiency, among which the anti-MAOs (anti-Monoamine oxidase), corticosteroids, diuretics. Zinc-deficiency can cause growth retardation, delayed sexual maturation, and longer times for wound-healing. Zinc-deficiency can also lead to atherosclerosis and increase susceptibility to infections. Stretch marks and nail white spots can be symptoms of zinc-deficiency. Other symptoms of zinc-deficiency are fragile nails and hair, lack of hair pigment, irregular menstrual cycles in adolescent girls, impotence in young males, and knee and hip joint pains in adolescents. Chronic zinc-depletion can even predispose body cells to cancer. Even small zinc-deficiencies are deleterious to the organism, for instance they can determine a reduction in the concentration of spermatozoa and impotence. Furthermore, zinc-deficiency causes fatigue, higher chances of contracting infections or experiencing wounds, and reduced mental agility. In fact, zinc-deficiency hinders energy production, protein synthesis, collagen formation, and alcohol tolerance.

Food or dietary compositions containing zinc in combination with pro-biotic agents are described in the prior art.

For Example, US patent application 20070009502 A describes nutritional compositions for animal feed, designed for the improvement or maintenance of the gastrointestinal microflora, comprising pro-biotic agents (such as yeast and/or bacteria, for Example *Bifidobacterium, Enterococcus* or *Lactobacillus*), pre-biotic agents, glutamine or its analogues, glucose, glycine, electrolytes, vitamins and minerals, including mineral zinc (100-200 mg/kg).

Patent application WO 2006/112998 describes a liquid nutritional supplement to be used in combination with human milk, designed to promote the growth of breast-fed babies suffering growth retardation, comprising numerous ingredients, among which pro-biotics (such as *Lactobacillus* and/or *Bifidobacterium*) and minerals, including zinc.

Patent application CA 2525342 A describes a broad-range pro-biotic food preparation useful in food supplements, for instance for improving the immune response against diseases, comprising specific bacterial strains of *Lactobacillus plantarum, Lactobacillus fermentum, Lactobacillus casei* sbp. *pseudoplantarum, Lactobacillus acidophilus* and *Lactobacillus casei*, in combination with further auxiliary components, linkers and energizing components, including zinc.

The above-mentioned prior documents describe compositions suitable for zinc delivery within the human or animal body, wherein zinc is in the form of inorganic zinc and is in combination with many other ingredients, including pro-biotic micro-organisms.

These compositions have the disadvantage that they contain zinc exclusively in the inorganic form, which is more difficult for the human body to absorb than organic zinc.

The inventors have now found that certain bacterial species belonging to the *Bifidobacterium* and *Streptococcus* genera, especially the *Bifidobacterium animalis* and *Streptococcus thermophilus* species, when grown on a culture medium containing inorganic zinc, display the unexpected and advantageous ability to accumulate extremely high quantities of zinc within the cell, without such high amounts of intracellular zinc which is deleterious for the survival of the biomass itself. Such a capacity to accumulate zinc intracellularly makes the aforesaid bacterial species particularly suitable for use as a zinc delivery means within the human or animal body, particularly useful for the manufacture of pro-biotic products that, by definition, must contain a living biomass. The zinc-enriched biomass of the invention may also be used in cosmetic applications, especially for the manufacture of cosmetic or cosmeceutic products. For the manufacture of cosmetic products, the biomass needs to be made up of dead micro-organisms, whereas for the manufacture of cosmeceutic products, the biomass needs to be made up of living micro-organisms.

Thus, one object of the invention is a method for the manufacture of a zinc-enriched biomass, characterised in that the biomass is obtained by (i) culturing micro-organisms selected from the group consisting of *Bifidobacterium animalis, Streptococcus thermophilus*, and combinations thereof, in a nutrient culture medium comprising a zinc salt, so that the said micro-organisms accumulate zinc at an intracellular level; and (ii) separating the zinc-enriched micro-organisms from the culture medium.

A biomass comprising living micro-organisms that contain a high quantity of zinc accumulated within the cells is achieved by the method of the invention, as is evident from the studies reported hereinafter.

The method for the manufacture of the zinc-enriched biomass of the invention provides for a first fermentation step, wherein the micro-organisms are cultured in a nutrient medium suitable for growing micro-organisms from the *Bifidobacterium* and *Streptococcus* genera supplemented with a zinc salt, preferably zinc sulphate ($ZnSO_4$). The nutrient medium is preferably a liquid medium containing carbon sources, for instance glucose and/or lactose; nitrogen sources, for Example peptones, casein hydrolysates, yeast extracts; inorganic salts; micro-elements and vitamin sources.

The concentration of the zinc salt in the culture medium is preferably between 5 and 50 mM, even more preferably between 10 and 40 mM.

Zinc sulphate is preferred.

The fermentation is preferably carried out at a temperature between 25° C. and 48° C., more preferably between 35° C. and 45° C. The pH value of the liquid medium preferably is between 2.5 and 8.0, more preferably between 3.5 and 7.5. The fermentation time length is preferably between 6 and 40 hours, more preferably between 8 and 36 hours. The fermentation may be carried out under aerobic, micro-aerobic, and/or anaerobic conditions.

Following the fermentation step, during which biomass growth and zinc accumulation within the bacterial cells occur, the biomass obtained is separated from the culture medium by any suitable per se known method, for Example by centrifugation or micro-filtration, in such a way as not to compromise the cell viability. Thus, the method of the invention allows a zinc-enriched micro-organism biomass to be obtained comprising living microorganisms. If desired, the biomass obtained may then be subjected to freeze-drying, drying, micro-encapsulation and/or freezing, carried out according to conventional procedures.

The present inventors have also selected two micro-organism strains from the *Streptococcus thermophilus* and *Bifidobacterium animalis* species, which proved to be particularly advantageous for use in the method of the invention, as they are endowed with a particularly high ability to accumulate zinc within the cell. Such strains have been designated as *Streptococcus thermophilus* ST 16 BM and *Bifidobacterium animalis* subsp. *lactis* BB 1 BM and have been deposited at the DSMZ (Deutsche Sammlung fur Mikroorganismen und Zellkulturen, Braunschweig, Germany), under the Budapest Treaty, as *Streptococcus thermophilus* ST 16 BM deposited on Jul. 13, 2007, under the accession number DSM 19526, and *Bifidobacterium animalis* subsp. *lactis* BB 1 BM deposited on Dec. 23, 2005, under the accession number DSM 17850, respectively.

As previously described, the zinc-enriched biomass achievable by the method of the invention is particularly suitable for use as a pro-biotic agent, in that it contains high zinc concentrations in the organic form.

To this end, the biomass comprising living micro-organisms, and therefore having probiotic activity, may be prepared in different forms. For instance, it can be added to a food product, preferably a milk or a dairy product such as yoghurt, in order to obtain a food preparation having pro-biotic activity. Alternatively, it may be used for the manufacture of a composition having pro-biotic activity, such as for Example a food supplement, a dietary product, a functional food, or for the manufacture of a non-food preparation for oral administration, such as for Example a nutraceutic product, in combination with suitable vehicles and/or excipients. To this end, the biomass is preferably used in the form of a freeze-dried or dried composition as such and/or of a micro-encapsulated composition.

The bacterial load of the freeze-dried or dried product to be subsequently used in the composition having pro-biotic activity is at least of $10^{10}$-$10^{11}$ CFU/g of product.

For the manufacture of the freeze-dried or dried product, the wet biomass is suspended in a liquid medium, for Example water or a sterile physiologic solution, with the inclusion of protective agents such as for Example skimmed milk, lactose, glucose, yeast extract, potato starch, sodium glutamate, inositol, sodium citrate, gelatine, maltodextrin, magnesium stearate, ascorbic acid, stearic acid and combinations thereof.

The freeze-dried or dried product is then diluted for the manufacture of pro-biotics with inert substances selected for Example from the ones indicated above for the freeze-drying, such as to obtain a bacterial load preferably of at least $10^9$ CFU/g of product. The freeze-dried product may be micro-encapsulated in order to increase the stability at room temperature (18-24 months).

For the manufacture of a product wherein the biomass must be dead (for instance a cosmetic product or some food products, such as bakery products), the zinc-enriched biomass achievable by the method of the invention is subjected to per se known methods, such as drying, to obtain dead cells.

Figure 1:
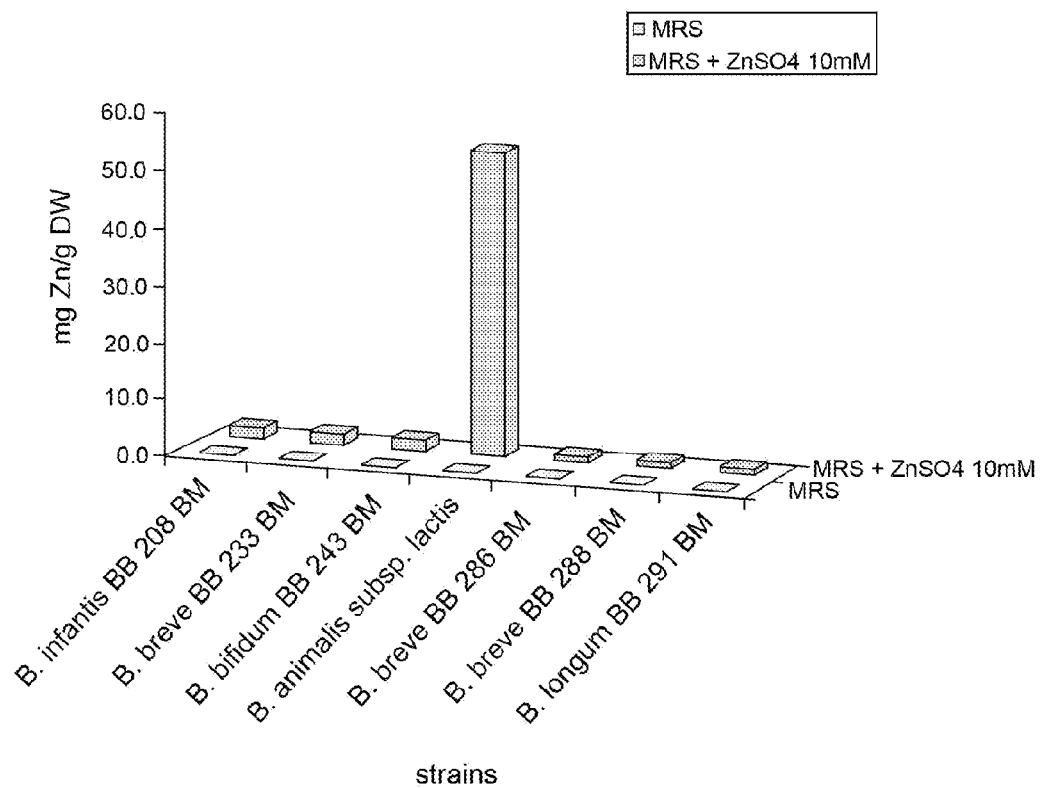
FIG. 1 shows a diagram reporting intercellular zinc concentrates measured in uptake tests carried out on strains of different species of *Bifidobacterium*.

The following experimental section is provided exclusively by way of illustration and is not intended to limit the scope of the invention as defined in the attached claims.

Tests of Intracellular Zinc Uptake

In order to compare the total intracellular zinc contents and to estimate the accumulation capacity of the metal at the cytoplasmic or membrane level, we carried out a screening on pro-biotic micro-organism strains grown on media with or without zinc sulphate.

*Bifidobacterium* cultures stored in MRS infission were inoculated into liquid MRS and anaerobically incubated at 37° C. After a 24 hour growth period, 120 ml (10% v/v) of liquid MRS alone and 120 ml (10% v/v) of liquid MRS supplemented with 10 mM $ZnSO_4$, were inoculated, respectively. These cultures were incubated under anaerobic conditions at 37° C. for 48 hours. The same experimental procedure was followed to set up tests of intracellular uptake in *Streptococcus*. In this case, a liquid M17 medium was used and the cultures were incubated under anaerobic conditions at 42° C. for 48 hours.

At the end of the growth, having kept a small aliquot for the determination of the dry weight, we proceeded to separate the biomass from the culture medium by centrifugation and to mineralize the collected biomass.

Biomass Mineralization

In order to determine the total intracellular zinc, the bacterial cells were completely disrupted and then the biomass was mineralized according to the protocol reported hereinafter.

One hundred ml of the grown cultures were centrifuged for 30 minutes at 4500 rpm (in a centrifuge cooled down to 4° C., Beckman GS-15R centrifuge) to collect the cells. The pellet was then washed 4 times, each time with 140 ml of distilled water, in order to eliminate the residual zinc from the supernatant. The fourth water wash was retained to analyze its zinc contents by the ICP technique.

The biomass was mineralized by re-suspending the pellet in a 1:1 ratio (w/v) with a solution of nitric acid $HNO_3$. During the optimization of the mineralization procedure, in order to achieve total recovery of the intracellular zinc, we used increasing concentrations of nitric acid solutions, 0.65%, 6.5%, and 20%, respectively.

Each so-obtained cell suspension was transferred into screw-cap tubes and stored at −20° C. for at least 2 hours. The screw-cap tubes were then thawed in a thermostat bath at 100° C. for 30 minutes under a chemical hood: to avoid excessive evaporation and pressure within the tubes, these were sealed with stoppers fitted with a vent needle. The solutions were cooled at room temperature, allowing for the reaction vapours to be given off. At the end of the mineralization procedure, the cell suspensions were centrifuged at 13000 rpm for 30 minutes at 4° C. in order to collect the mineralized extract and to eliminate the cell debris.

Total Zinc Analysis by ICP

For the analysis by ICP, the samples were acidified at 2% with 65%-concentrated $HNO_3$ and then diluted with bi-distilled water up to a 5 ml final volume. These operations were effected under a chemical hood. The solutions thus obtained were filtered by using 0.8 µm cellulose acetate filters (Millex-AA, Millipore) until they were completely clear.

The quantification of the intracellular zinc accumulated by the strains under examination was carried out by the ICP-AES technique (OES-OPTIMA 4200 DV, Perkin Elmer).

The system uses frequencies of 40 MHz. The plasma injection is automated and controlled by a computer-connected electronic system.

The argon used must be 99.99% pure and its flow must always be in a range from 0 to 20 liters/minute, with variable increases of 1 liter/minute. The nebulised sample flow must occur within mass flow values from 0 to 0.01 liters/minute, with variable increases of 1 liter/minute.

The nebuliser is made up of corrosion-resistant materials, so the system can withstand solutions with 50% (v/v) concentrations of HCl, $HNO_3$, $H_2SO_4$, $H_3PO_4$, 30% (v/v) concentrations of NaOH and 20% (v/v) concentrations of HF.

The spectrophotometer consists of a polycromator that lies in a thermostat compartment at 38° C. The detection method used is the CCD and the reading out is done in the UV field.

Analysis Parameters Used:
Resolution: high
Purge gas flow: normal
Read delay time (sec): 45
Replicates: 3
Read time: auto
Min. time: 1.000 sec.-Max. time: 10.000 sec.
Source equilibration delay: 15 sec.
Plasma aerosol type: wet
Nebulizer start-up conditions: instant In order to obtain the unknown zinc concentration, we used a calibration line constructed with the following standard solutions 2% acidified with $HNO_3$: 0.5 ppm, 1 ppm, 2 ppm, and 10 ppm zinc.

The total cell zinc is expressed in mg of metal per gram of dry biomass.

The total intracellular concentration of the accumulated metal was defined by the ICP-AES technique described above by acidifying the samples obtained at 2% with $HNO_3$.

FIG. 1 reports the intracellular zinc concentrations (expressed as mg of intracellular zinc per gram of dry cell weight) measured in uptake tests carried out on strains of different species of Bifidobacterium. Specifically, the tests were effected on strains of B. infantis, B. breve, B. bifidum, B. animalis, B. longum. All the analysed strains show a very low intracellular zinc concentration, with values lying between 0.01 and 0.20 $mg/g_{DW}$, when grown on zinc-free MRS medium. The addition to the MRS culture medium of 10 mM zinc sulphate induces an increase in the intracellular zinc concentration. However, as can be seen from FIG. 1, the concentrations of the internalised metal are rather low and lie between 0.72 $mg/g_{DW}$ and 2.12 $mg/g_{DW}$ in the strains of all species, except for the Bifidobacterium animalis subsp. lactis BB 1 BM strain (accession number DSM 17850; filing date Dec. 23, 2005) wherein the intracellular zinc concentration increases up to 53.32 $mg/g_{DW}$ (an increase of as much as 1.000 times the basal concentration).

Figure 2:
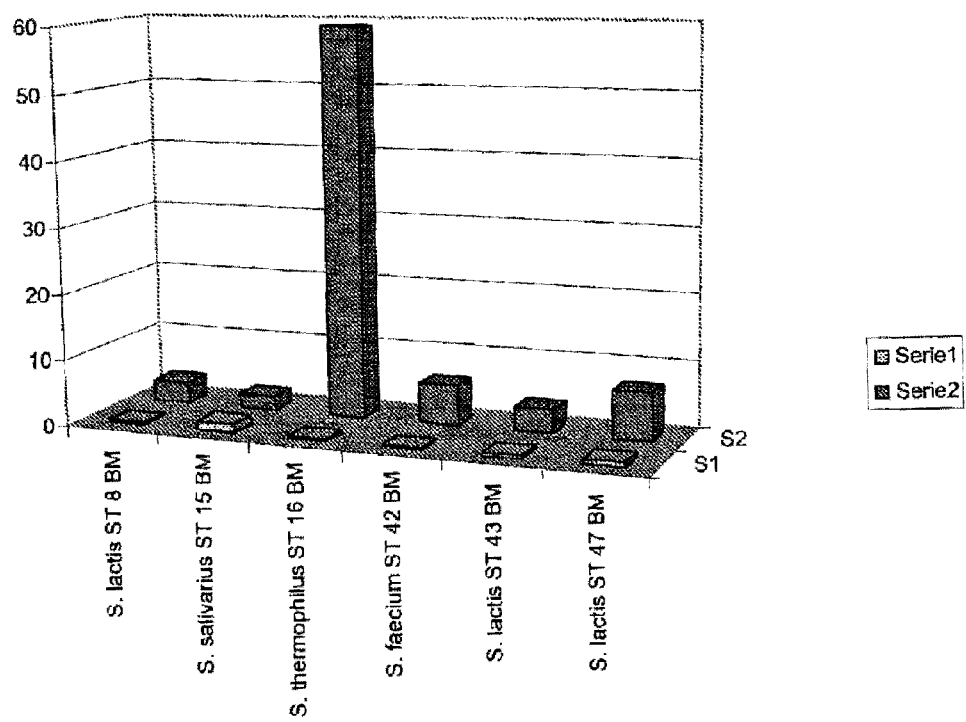
FIG. 2 shows intracellular zinc values achieved with *Streptococcus thermophilis* ST and other strains belonging to the *Streptococcus* species, such as *S. salivarius*, *S. faecium*, and *S. lactis*.

As can be seen from FIG. 2, comparable intracellular zinc values have been achieved with the Streptococcus thermophilus ST 16 BM strain (accession number DSM 19526; filing date Jul. 13, 2007) grown on M17 medium enriched with 10 mM zinc sulphate (intracellular zinc concentration=59.31 $mg/g_{DW}$) (Series 1). FIG. 2 further shows that strains belonging to other Streptococcus species, such as S. salivarius, S. faecium and S. lactis, demonstrate an much lower ability to accumulate intracellular zinc when grown on the same medium. Furthermore, the figure shows the comparison with the intracellular zinc concentrations detected when the strains are grown on the same M17 medium without zinc sulphate added (Series 2).

Example 1

200 ml of M17 medium (Merck), to which 10 mM zinc sulphate has been added, were sterilised in a 500 ml flask. A seed culture of Streptococcus thermophilus ST 16 BM (accession number DSM 19526; filing date Jul. 13, 2007), previously grown for 24 hours at 42° C. under anaerobic conditions, was inoculated into the flask in the amount of 10% (v/v). The culture was then left growing for 40 hours at 42° C. under anaerobic conditions. $2.73 \times 10^9$ CFU/ml were obtained at the end of the culture. The biomass was collected by centrifugation and treated and analysed according to the methods described above. The total zinc accumulated by the cells was 59.31 $mg/g_{DW}$. D.W.=dry weight.

Example 2

As in Example 1, using SBF31 medium+15 mM $Zn^{2+}$ separately sterilised by filtration. SBF31 medium: tryptone 23 g/l; soybean peptone 16 g/l; yeast extract 12 g/l; $MgSO_4$ 0.25 g/l; $K_2HPO_4$ 2.5 g/l; ascorbic acid 0.5 g/l; glucose 45 g/l; Na diglycerophosphate 19 g/l.

Fermentation time: 21 hours; production of living cells: $5.3 \times 10^{10}$ CFU/ml; accumulated zinc: 51.67 $mg/g_{DW}$.

Example 3

As in Example 1, using SBF32 medium+30 mM $Zn^{2+}$ separately sterilised by filtration. After 21 hours, 2.1 g/liter of dry biomass having a viability of $3.15\times10^{10}$ CFU/ml was obtained; accumulated zinc: 63.42 $mg/g_{DW}$. SBF32 medium: tryptone 23 g/l; soybean peptone 16 g/l; yeast extract 12 g/l; $MgSO_4$ 0.25 g/l; $K_2HPO_4$ 2.5 g/l; ascorbic acid 0.5 g/l; lactose 45 g/l; glycerine 19 g/l.

Example 4

71 ml of M17 medium, to which 10 mM zinc sulphate has been added (separately sterilised by filtration) were inoculated with 500 ml of seed culture liquor from the same M17 medium+10 mM zinc sulphate into which *Streptococcus thermophilus* ST 16 BM (accession number DSM 19526; filing date 13 Jul. 2007) has previously been grown for 24 hours at 42° C. under anaerobic conditions. Fermenter conditions: 150 rpm; 0.5 l air/1/min; temperature: 42° C.; pH adjusted to 4.8 (±0.2) with 10% NaOH; fermentation time: 21 hours. $2.75\times10^{10}$ CFU/ml were obtained. The total zinc accumulated by the cells was 57.2 $mg/g_{DW}$.

Example 5

As in Example 4, but two additions of 15 mM $Zn^{2+}$ were made during fermentation at log 12 and log 18. Fermentation time: 24 hours. Cell viability at the end of the fermentation: $2.25\times10^{10}$ CFU/ml. The total zinc accumulated by the cells was 91.3 $mg/g_{DW}$.

Example 6

300 ml of MRS medium (Merck)+cysteine, sterilised at 120° C. for 30 minutes, to which filter-sterilised 10 mM zinc sulphate has been added, were kept in pre-reduction for not less than 24 hours under aerobic environment. A *Bifidobacterium animalis* subsp. *lactis* BB 1 BM (accession number DSM 17850; filing date Dec. 23, 2005) seed culture liquor, previously grown for 24 hours in the same medium under anaerobic conditions at 37° C., was inoculated into the abovementioned 300 ml at 10% (v/v) and grown under anaerobic conditions for 24 hours at 37° C. $1\times10^{11}$ CFU/ml were obtained at the end of the culture. The total zinc accumulated by the cells was 53.32 $mg/g_{DW}$.

Example 7

A 15 liter anaerobic fermenter fitted with a shaker plate in place of the shaft was prepared with 10 liters of medium and in the same conditions as in Example 6. Zinc sulphate was adjusted to 15 mM. The fermenter was inoculated with 10% v/v of a 24 hour *Bifidobacterium animalis* subsp. *lactis* BB 1 BM (accession number DSM 17850; filing date Dec. 23, 2005) seed culture liquor and incubated at 37° C. for 24 hours. The amount of living cells was $1\times10^{11}$ CFU/ml. The total zinc accumulated by the cells was 67.1 $mg/g_{DW}$.

Example 8

90 ml of MRS medium containing 0.05% cysteine, to which 10 mM Zn sulphate has been added, were sterilised in a 100 ml flask. A *Bifidobacterium animalis* subsp. *lactis* BB 1 BM seed culture, previously grown for 24 hours at 37° C. under anaerobic conditions in the same medium, was inoculated into the flask in the amount of 10% v/v. The culture was then left growing for 40 hours at 37° C. under anaerobic conditions. $3.12\times10^9$ CFU/ml were obtained at the end of the culture. The biomass was collected by centrifugation and treated and analysed according to the disclosed method. The total Zn accumulated by the cells was 54.36 mg/g p.s.

Example 9

90 ml of minimal basal medium (in grams per liter) were formulated as follows: Casamino acids (Difco Laboratories, Sparks, Md.), 15; yeast nitrogen base (Difco Laboratories), 6.7; ascorbic acid, 10; sodium acetate, 10; $(NH_4)_2SO_4$, 5; urea, 2; $MgSO_4.7H_2O$, 0.2; $FeSO_4.7H_2O$, 0.01; $MnSO_4.7H_2O$, 0.007; NaCl, 0.01; Tween 80, 1; cysteine, 0.5 (pH adjusted to 7.0 and autoclaved for 30 minutes at 110° C.). One of the following carbohydrates (glucose, fructo-oligosaccharides, inulin, raffinose, lactose, galacto-oligosaccharides, fructose, galactose or xylo-oligosaccharides) was autoclaved separately and added to the basal medium in order to achieve a 10 g/l concentration. 10 mM Zn sulphate was further added. A *Bifidobacterium animalis* subsp. *lactis* BB 1 BM seed culture, previously grown for 24 hours at 37° C. under anaerobic conditions in the same medium, was inoculated into the flask in the amount of 10% v/v. The culture was then left growing for 40 hours at 37° C. under anaerobic conditions. Biomass concentrations in the range from $1.5\times10^8$ CFU/ml to $3.2\times10^9$ CFU/ml were obtained at the end of the culture. The biomass was collected by centrifugation and treated and analysed according to the method described. The total zinc accumulated into the cells was in the range from 48.12 to 54.37 mg/g p.s.

Example 10

2 liters of MRS medium containing 0.05% cysteine and added with 10 mM Zn sulphate, were sterilised in a 3.6 liter bioreactor and inoculated at 10% with a *Bifidobacterium animalis* subsp. *lactis* BB 1 BM culture grown for 24 hours in the same medium. The bioreactor was sterilised in situ and pressurized with nitrogen. The process conditions were: constant nitrogen insufflation at 0.01, 150 rpm, 37° C., pH maintained at 6.2 with 0.1 M NaOH. After 48 hours the biomass had a concentration of $3.6\times10^9$ CFU/ml. The biomass was collected and analysed for the amount of zinc. The total zinc accumulated into the cells was 53.81 mg/g p.s.

Example 11

2 liters of MRS medium containing 0.05% cysteine were sterilised in a 3.6 liter bioreactor and inoculated at 10% with a *Bifidobacterium animalis* subsp. *lactis* BB 1 BM culture grown for 24 hours in the same medium. The bioreactor was sterilised in situ and pressurized with nitrogen. The process conditions were: constant nitrogen insufflation at 0.01, 150 rpm, 37° C., pH maintained at 6.2 with 0.1 M NaOH. After a 24 hour growth period, Zn sulphate was added to the culture in order to achieve a 10 mM final concentration. 24 hours from the addition of the metal, the biomass had a concentration of $3.6\times10^9$ CFU/ml. The biomass was collected and analysed for the amount of zinc. The total zinc accumulated into the cells was 53.81 mg/g p.s.

Example 12

10 liters of MRS medium containing 0.05% cysteine with an addition of 10 mM Zn sulphate, were sterilised in a 3.6 liter bioreactor and inoculated at 10% with a *Bifidobacte-*

*rium animalis* subsp. *lactis* BB 1 BM culture grown for 24 hours in the same medium. The bioreactor was sterilised in situ and pressurized with nitrogen. The process conditions were: constant nitrogen insufflation at 0.01, 150 rpm, 37° C., pH maintained at 6.2 with 0.1 M NaOH. After the culture had finished acidifying, as indicated by the termination of NaOH attraction, the culture was supplied in fed-batch mode with a 30% glucose and 10 mM Zn sulphate solution. After having reached a 15 liter volume, the biomass had a concentration of $1.2 \times 10^{10}$ CFU/ml and was collected and analysed for the amount of zinc. The total zinc accumulated into the cells was 52.15 mg/g p.s.

The invention claimed is:

1. A zinc-enriched biomass, obtainable by a method comprising:
   (i) culturing micro-organisms selected from the group consisting of *Bifidobacterium animalis, Streptococcus thermophilus*, and combinations thereof, in a nutrient culture medium comprising a zinc salt in a concentration between 5 to 50 mM, to obtain zinc-enriched micro-organisms wherein the zinc-enriched micro-organisms accumulate at least 50 $mg/g_{DW}$ intracellular zinc; and
   (ii) separating the zinc-enriched micro-organisms from the culture medium,
      wherein the micro-organisms are selected from the group consisting of *Streptococcus thermophilus* ST 16 BM, deposited under the Budapest Treaty at the DSMZ, Braunschweig, Germany, under the accession number DSM 19526 on Jul. 13, 2007, and *Bifidobacterium animalis* subsp. *lactis* BB 1 BM, deposited under the Budapest Treaty at the DSMZ, Braunschweig, Germany, under the accession number DSM 17850 on Dec. 23, 2005.

2. The zinc-enriched biomass according to claim 1, wherein the micro-organisms separated from the culture medium are freeze-dried, dried, microencapsulated and/or freezed.

3. The zinc enriched biomass according to claim 1, wherein the zinc salt is zinc sulphate.

4. The zinc enriched biomass according to claim 3, wherein the nutrient culture medium comprises a zinc sulphate amount in the range from 5 to 50 mM.

5. The zinc enriched biomass according to claim 1, wherein the culture medium is a liquid medium.

6. The zinc enriched biomass according to claim 1, wherein the culture medium comprises conventional nutrients for the growth of said micro-organisms, selected from the group consisting of carbon, nitrogen, vitamins, and additional inorganic salts and micro-nutrient sources, and mixtures thereof.

7. The zinc enriched biomass according to claim 1, wherein said culture medium has a pH in the range from 2.5 to 8.0.

8. The biomass according to claim 1, the biomass comprising living micro-organisms.

9. A pro-biotic agent comprising the biomass according to claim 8.

10. The biomass according to claim 1, comprising dead micro-organisms.

11. A composition having pro-biotic activity comprising the zinc-enriched living biomass according to claim 8, in combination with suitable vehicles and/or excipients.

12. The composition according to claim 11 with a bacterial load of at least $10^9$ CFU/g.

13. A food preparation, food supplement, dietary product, functional food, nutraceutic product, or cosmeceutic product, comprising the composition according to claim 11.

14. A cosmetic or food product comprising the biomass according to claim 10.

15. The zinc enriched biomass according to claim 1, wherein the zinc salt is in a concentration between 10 to 40 mM.

* * * * *